United States Patent [19]

Jessel, Jr. et al.

[11] Plant 4,153

[45] Nov. 22, 1977

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 716,440

[22] Filed: Aug. 23, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum plant having flat inflorescence form and anenome inflorescence type; medium yellow ray floret color with minimal oxidation; uniform eight week response; short plant height and semi-upright branching pattern.

3 Drawing Figures

1

The present invention comprises a new and distinct cultivar of *Chrysanthemum morifolium,* Ramat., hereinafter referred to by the cultivar name Joy (No. 70010C05).

Joy is a product of a planned sport induction program which had the objective of creating new chrysanthemum cultivars with anenome type inflorens, uniform 8 and 9 week flowering response, yellow and bronze inflorescence color, and high grade-out (Society of American Florist standards).

Joy is an induced sport of No. 70010005, (unnamed seedling). Joy was discovered and selected by Walter H. Jessel, Jr. and William E. Duffett on Jan. 1, 1975 as one plant within a flowering block of the parental cultivar in a controlled environment in Barberton, Ohio. Plants within the flowering block were derived from stock plants which had been irradiated as rooted cuttings with an x-ray source of 1800 *r.* units.

The parental cultivar of Joy, No. 70010005, was originated by the present inventors in 1969 as a product of a controlled breeding program. The female, or seed parent of No. 70010005 was No. 67100005 (unnamed seedling), a yellow daisy originated by the present inventors in 1966 from a cross between Tuneful (No. 54285007; unpatented, commercially available) and No. 65741001 (unnamed seedling). The male, or pollen parent, of No. 70010005 was Topflight (No. 21580E01; unpatented; commercially available), a yellow anemone originated by the present inventors in 1953 from a cross between No. 521258-3 (unnamed seedling) and Sunray (No. 21068E01; unpatented; commercially available). Tuneful, No. 65741001, and No. 521258-3 were products of the breeding program of the present inventors. The parentage of Sunray is unknown to the present inventors.

The first act of asexual reproduction of Joy was accomplished when vegetative cuttings were taken from the initial selection in July, 1975 in a controlled environment in Barberton, Ohio by a technician working under formulations established and supervised by Walter H. Jessel, Jr. and William E. Duffett. Horticultural examination of selected units initiated Mar. 9, 1976 has demonstrated that the combination of characteristics as herein disclosed for Joy are firmly fixed and are retained through successive generations of asexual reproduction.

Joy has not been observed under all possible environmental conditions. The phenotype may vary significantly with variations in environment such as temperature, light intensity and daylength. The following observations, measurements, and comparisons describe plants grown in Barberton, Ohio under greenhouse conditions which approximate those generally used in commercial practice, as described in Chart A which appears at the end of the present specification. A light intensity chart of general is shown in ASHAE Trans., Vol. 64, pg. 64, and reference is made thereto.

2

The following traits have been repeatedly observed and are determined to be basic characteristics of Joy which in combination distinguish this chrysanthemum as a new and distinct cultivar:

1. Flat inflorescence form.
2. Anenome inflorescence type.
3. Medium yellow ray floret color, tinging light bronze with cool (below 60° F) finishes.
4. Minimal inflorescence color oxidation during high temperature periods.
5. Uniform eight week flowering response to photoperiodic short-day control.
6. Short plant height (requiring 2–3 long day weeks prior to short days to attain a flowered plant height of 72 to 82 cm. when grown as a single stem plant from May through October).
7. Semi-upright branching pattern.
8. Diameter across face of inflorescence up to 95 mm. at maturity.

The accompanying photographic drawings show typical inflorescence and foliage characteristics of Joy. Sheet 1 is a color photograph of Joy. Sheet 2 is a black and white photograph showing three views of the inflorescence of Joy. Sheet 3 is a black and white photograph of the foliage of Joy at three stages of growth.

Of the many commercial cultivars known to the present inventors, the most similar existing cultivars in comparison to Joy are Florida Marble (No. 54318G08; U.S. Plant Pat. No. 3,288) and Cavalier (No. 62527004; unpatented). Reference is made to attached Chart B which compares certain characteristics of Joy, Florida Marble, and Cavalier. To summarize:

1. In comparison to Florida Marble, Joy has darker ray floret color, smaller diameter across face of inflorescence, different inflorescence color retention, shorter plant height, shorter flowering response, and different inflorescence type. The inflorescence form of Joy is similar to that of Florida Marble.

2. In comparison to Cavalier, Joy has smaller diameter across face of inflorescence, different inflorescence color, shorter plant height, and shorter flowering response. The ray floret color, inflorescence form, and inflorescence type of Joy are similar to those same characteristics of Cavalier.

In the following description, color references are made to The Munsell Limit Color Cascade, 1972 edition. The color values were determined between 8:00 A.M. and 8:30 A.M. on May 5, 1976 under 150 foot-candle light intensity at Barberton, Ohio.

Botanical Classification: *Chrysanthemum morifolium,* Ramat. cv Joy.

*Color (mature).*—27-6.

Reproductive organs:

*Androecium.*—Numerous; scant pollen.

*Gynoecium.*—Present both ray and disc florets.

Plant (see Sheet 1 of drawings)

General appearance: semi-upright branching pattern; short height.

Foliage (see Sheets 1 and 3 of drawings):

*Color (abaxial).*—20-15.

*Color (adaxial).*—20-14.

CHART A
AVERAGE GREENHOUSE CHRYSANTHEMUM ENVIRONMENTS USED FOR BARBERTON, OHIO

| | TEMPERATURES USED | | | | | |
|---|---|---|---|---|---|---|
| SEASON | Night | Bright Day | Cloudy Day | LIGHTING USED | BLACK CLOTH USED | SUPP $CO_2$ |
| FALL | 65° F to 56° F | 65° F to 80° F | 60° F to 75° F | 2 to 4 weeks at 3 Hours Per Night of 7-10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7-10 f.c. | NONE | 300 ppm |
| SPRING | 58° F to 65° F | 65° F to 80° F | 60° F to 75° F | 2 to 4 weeks at 5 Hours Per Night of 7-10 f.c. | From Mar. 15 on - 5:30 PM Off - 7:30 AM | to Apr. 15 300 ppm |
| SUMMER | 62° F to 68° F | 70° F to 90° F | 65° F to 75° F | 1 to 2 weeks at 3 Hours Per Night of 7-10 f.c. | on - 6:00 PM Off - 8:00 AM | NONE |

CHART B.
COMPARISON OF JOY, FLORIDA MARBLE AND CAVALIER

| CULTIVAR | RAY FLORET COLOR | DIAMETER ACROSS FACE OF INFLORESCENCE | INFLORESCENCE COLOR RETENTION | PLANT HEIGHT | FLOWERING RESPONSE | INFLORESCENCE FORM & TYPE |
|---|---|---|---|---|---|---|
| Joy | Medium Yellow | 60 to 95 mm. | Good | Short | 8 week | Flat Anenome |
| Florida Marble | Light Yellow | 70 to 85 mm. | Poor | Medium | 9 week | Flat Daisy |
| Cavalier | Medium Yellow | 75 to 95 mm. | Medium | Medium | 9 week | Flat Anenome |

COMPARISONS MADE OF PLANTS GROWN IN A GREENHOUSE IN BARBERTON, OHIO UNDER CONDITIONS DESCRIBED IN CHART A.

INFLORESCENCE (see Sheets 1 and 2 of drawings).

Capitulum

*Form.*—flat.

*Type.*—Anenome.

*Diameter across face.*—60 to 95 mm.

*Permanence.*—10 to 14 days.

Corolla of ray florets:

*Color (abaxial).*—26-6 to 26-4 tinging with cool temperature finishes to 31-11 over 26-6.

*Color (adaxial).*—31-11 streaked lightly over 26-4.

Corolla of disc florets:

*Color (immature).*—24-10.

We claim:

1. A new and distinct cultivar of *Chrysanthemum morifolium,* Ramat., plant known by the cultivar name Joy and particularly characterized as to uniqueness by the combined characteristics of flat inflorescence form; anenome inflorescence type; medium yellow ray floret color, tinging light bronze with cool (below 60° F) finishes; minimal inflorescence color oxidation during high temperature periods; uniform 8 week flowering response to photoperiodic short-day control; short plant height; semi-upright branching pattern; and diameter across face of inflorescence up to 95 mm. at maturity.

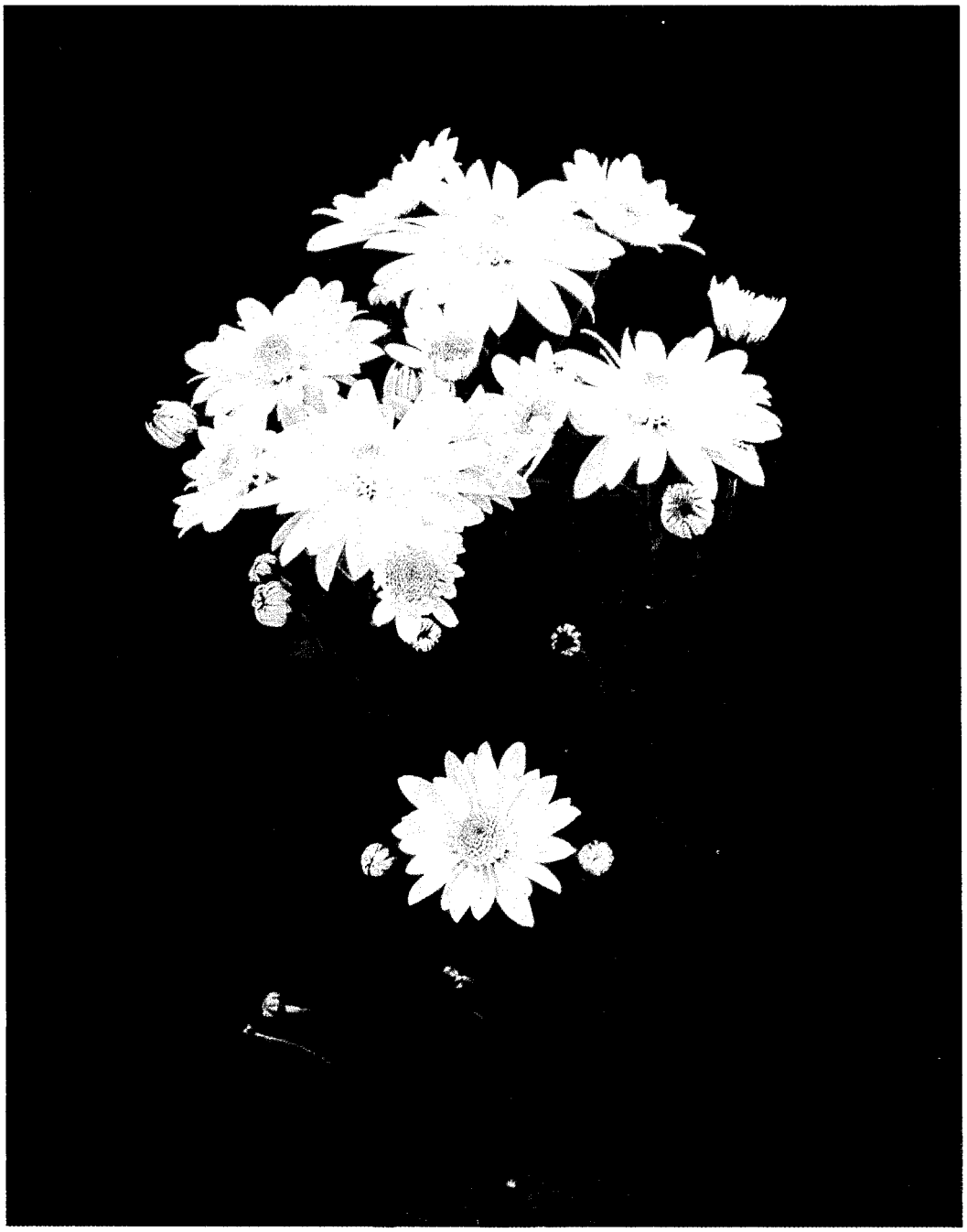

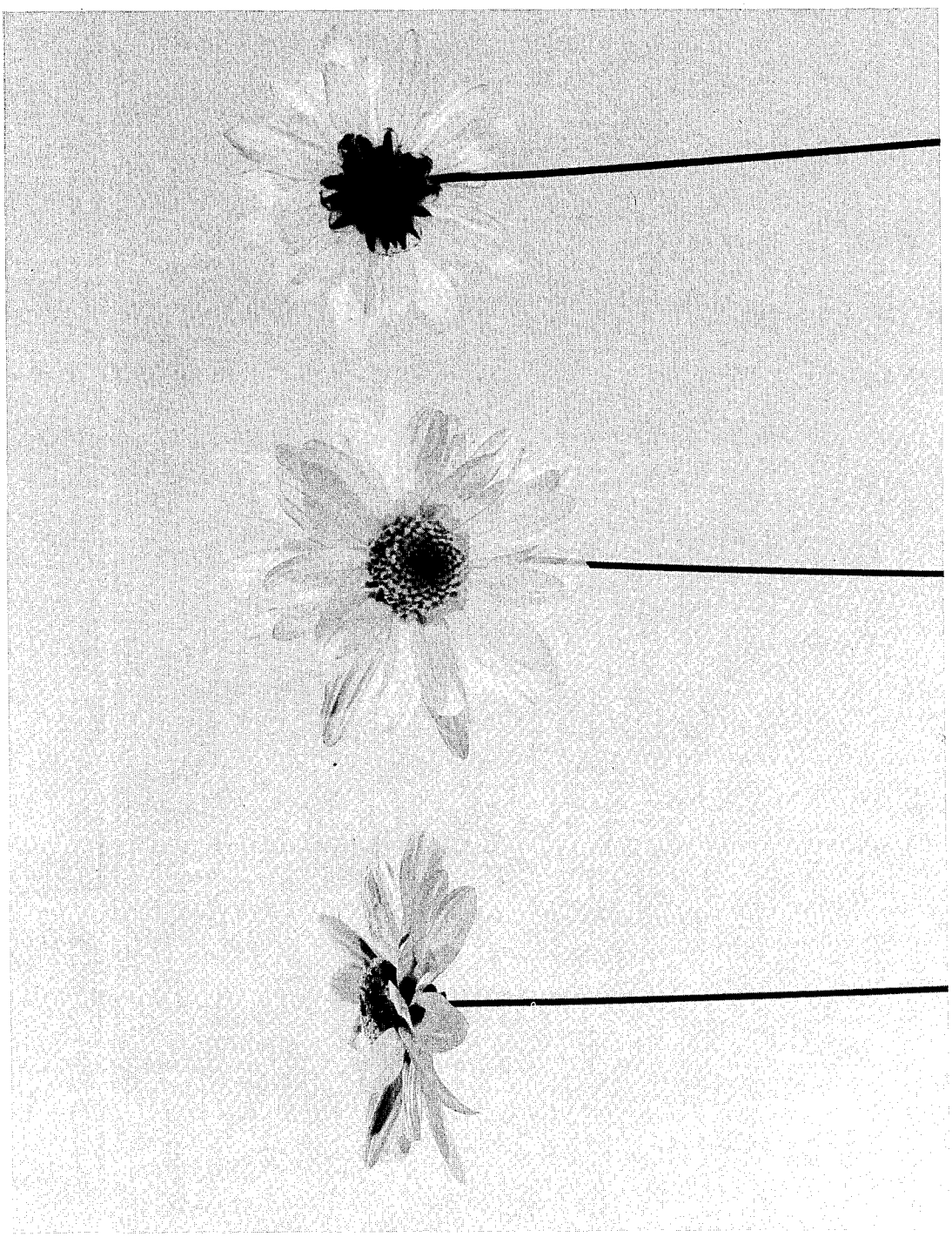

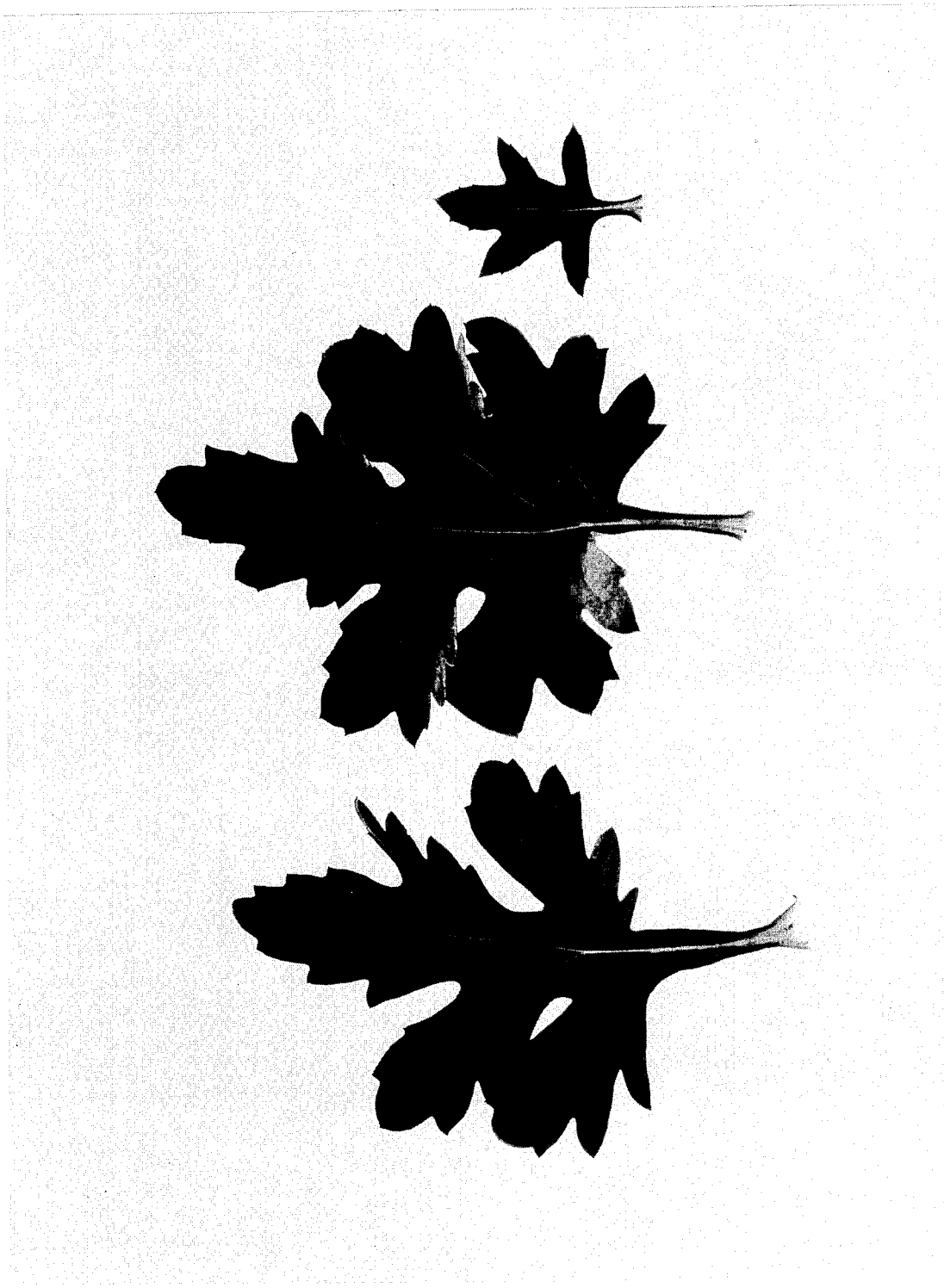

* * * * *